United States Patent [19]

Guglielmetti

[11] Patent Number: 5,332,861
[45] Date of Patent: Jul. 26, 1994

[54] PROCESS FOR PREPARING DISTYRYLBIPHENYL COMPOUNDS

[75] Inventor: Leonardo Guglielmetti, Bottmingen, Switzerland

[73] Assignee: Ciba-Geigy Corporation, Ardsley, N.Y.

[21] Appl. No.: 114,129

[22] Filed: Aug. 30, 1993

[30] Foreign Application Priority Data

Sep. 3, 1992 [CH] Switzerland ............ 2764/92

[51] Int. Cl.$^5$ ............ C07C 247/00
[52] U.S. Cl. ............ 562/87
[58] Field of Search ............ 562/87

[56] References Cited

U.S. PATENT DOCUMENTS

| | | | |
|---|---|---|---|
| 3,980,713 | 9/1976 | Matsunaga et al. | 562/87 |
| 3,984,399 | 10/1976 | Weber | 260/240 |
| 4,147,648 | 4/1979 | Günter et al. | 562/87 |
| 4,925,595 | 5/1990 | Hefti et al. | 562/87 |
| 5,145,991 | 9/1992 | Weber | 562/87 |
| 5,177,255 | 1/1993 | Bader et al. | 562/87 |

FOREIGN PATENT DOCUMENTS

| | | | |
|---|---|---|---|
| 0298361 | 1/1989 | European Pat. Off. | 562/87 |
| 0364403 | 4/1990 | European Pat. Off. | 562/87 |
| 1793482 | 3/1972 | Fed. Rep. of Germany | 562/87 |

*Primary Examiner*—Dees: Jose' G.
*Assistant Examiner*—Keith MacMillan
*Attorney, Agent, or Firm*—Kevin T. Mansfield; Edward McC.Roberts

[57] ABSTRACT

Process for preparing distyrylbiphenyl compounds by condensation of a substituted or unsubstituted 4,4'-bis(-dialkoxyphosphonomethyl)biphenyl compound with a substituted or unsubstituted benzaldehyde in liquid ammonia as the solvent and in the presence of strong bases; and the use of these distyrylbiphenyl compounds as fluorescent whitening agents.

16 Claims, No Drawings

PROCESS FOR PREPARING DISTYRYLBIPHENYL COMPOUNDS

The application relates to a novel process for preparing distyrylbiphenyl compounds.

Processes for preparing distyrylbiphenyl compounds via the Wittig-Horner reaction are generally known, for example from DE-A-1793482. Of the reaction solvents proposed there, only dimethylformamide and dimethyl sulfoxide have found practical application (EP-A-364403) and of the bases proposed, only sodium methoxide is generally used today.

However, the use of dimethylformamide as the reaction solvent has great disadvantages. Thus, dimethylformamide is, for example, known to be unstable in the presence of bases. Under the reaction conditions used in practice, a small portion of the dimethylformamide is hydrolysed by sodium methoxide. The resulting dimethylamine causes not only ecological problems but also gives the distyrylbiphenyl compound isolated an unpleasant dimethylamine odour which is difficult to remove. Furthermore, the base used (sodium methoxide) has poor solubility in dimethylformamide so that in practice the base is used in the form of a 30% methanolic sodium methoxide solution. This procedure has the disadvantage that two solvents (dimethylformamide and methanol) have to be regenerated. Since dimethylformamide is an aprotic dipolar solvent of high boiling point (154° C.), it can only be regenerated in practice at a loss of 5 to 10%.

The use of dimethyl sulfoxide as reaction solvent has similar disadvantages. It is true that dimethyl sulfoxide, in contrast to dimethylformamide, is stable in the presence of bases, and the base used (sodium methoxide) is readily soluble in dimethyl sulfoxide. However, dimethyl sulfoxide is not stable to oxidation/reduction reactions, which result in the formation of dimethyl sulfide, dimethyl disulfide and, in particular, methyl mercaptan which has a very unpleasant odour. Furthermore, dimethyl sulfoxide has a boiling point of 189° C. and can therefore also only be regenerated in practice at a loss of 5 to 10%, the losses being in this case more significant owing to the costs which are twice as high compared with dimethylformamide.

When the abovementioned reaction is carried out using one of the abovementioned solvents and sodium methoxide as the base, the workup also involves great disadvantages. After most of the solvent used has been recovered, the condensation mass must first be dissolved in water and the solution be clarified by filtration in order to permit isolation of the condensation product in a sufficiently pure state by crystallization. Since Wittig-Horner reactions produce not only the desired condensation product but also equimolar amounts of the corresponding salt of the dialkyl phosphate, the abovementioned operations, owing to the strong salting-out effect of this phosphoric acid salt, have to be carried out in strong dilutions. Accordingly, after isolation of the distyrylbiphenyl compound, large amounts of highly dilute mother liquors containing dialkyl phosphate have to be disposed of.

It has now been found that distyrylbiphenyl compounds of the formula (1)

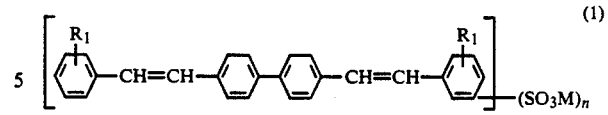

can be prepared by condensation of a compound of the formula (2)

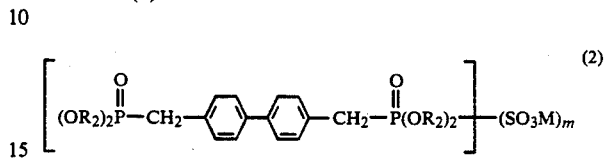

with a compound of the formula (3)

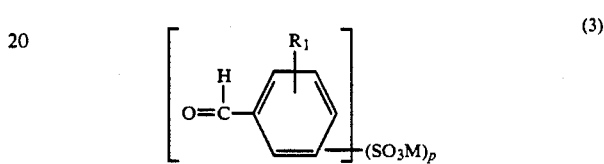

in which $R_1$ is hydrogen, $C_1$-$C_5$alkyl or halogen;
$R_2$ is $C_1$-$C_8$alkyl;
M is a salt-forming colourless cation;
n is 2 or 4;
m is 0 or 2; and
p is 0 or 1; provided m+p is 2 or 4, by carrying out the condensation in liquid ammonia and in the presence of strongly alkaline substances.

Examples of radicals $R_1$ are hydrogen, methyl, ethyl, propyl, butyl, t-butyl, propyl, chlorine or bromine, hydrogen, methyl, ethyl and chlorine being preferred. The radicals $R_2$ used are usually methyl, ethyl, propyl, butyl, hexyl or octyl, methyl, ethyl, propyl and butyl being preferred.

Examples of cations M are alkali metal cations, such as sodium and potassium, alkaline earth metal cations, such as calcium and magnesium, and ammonium cations.

The reactants preferably used for the condensation are the compounds of the formulae (4) and (5)

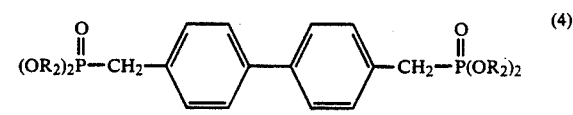

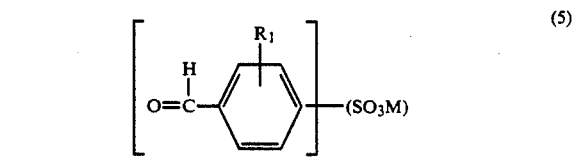

in which $R_1$ is hydrogen, $C_1$-$C_5$alkyl or halogen;
$R_2$ is $C_1$-$C_8$alkyl, and
M is a salt-forming colourless cation.

In a particularly preferred process, the compounds of the formulae (4) and (6)

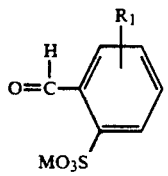

in which
R$_1$ is hydrogen, C$_1$-C$_5$alkyl or chlorine;
R$_2$ is C$_1$-C$_8$alkyl; and
M is a salt-forming colourless cation, are condensed.

The starting compounds of the formula (2) are disclosed, for example, in DE-A-1793482 and can in general be obtained by reaction of 4,4'-bis(chloromethyl)-biphenyl derivatives with alkyl phosphites, such as trimethyl phosphite, by the method of Arbuzov.

The compounds of the formula (3) can be prepared, for example, by reaction of chlorinated benzaldehydes with sodium sulfite in water and under pressure.

The process according to the invention provides in particular the compounds of the formulae (7)–(12)

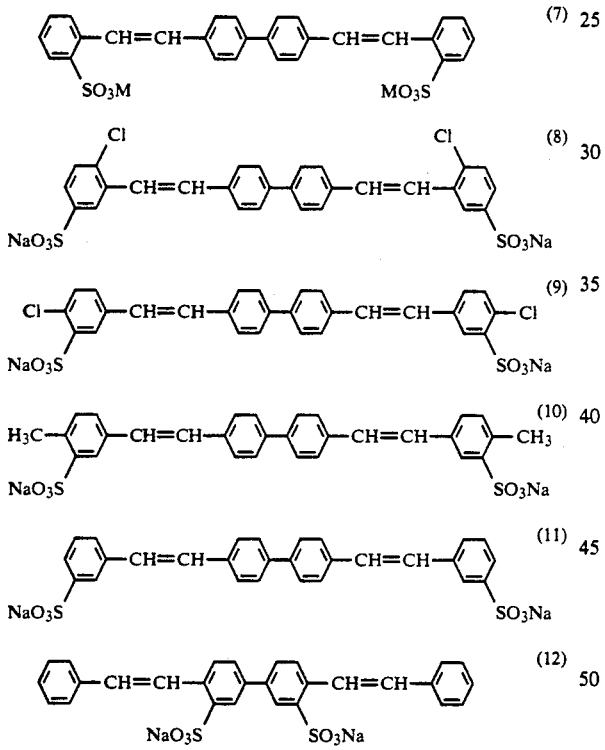

According to the invention, the condensation is carried out in liquid ammonia, for example at temperatures of between −40° C. and 25° C., preferably between 0° C. and 25° C., and particularly preferably between 10° C. and 20° C., in the presence of strong bases. Since ammonia has a boiling point of −33.35° C. (760 mmHg), it follows that at temperatures higher than this the reaction must be carried out at superatmospheric pressure.

Examples of strongly alkaline substances suitable for the condensation reaction are alkali metals or alkaline earth metals, such as lithium, sodium, potassium, magnesium and calcium and their strongly basic compounds, for example hydroxides, amides or alcoholates, and strongly basic ion exchangers. The alcoholates used are essentially those derived from open-chain, branched or cyclic lower aliphatic alcohols having 1 to 8 carbon atoms, preferably 1 to 4 carbon atoms, such as methanol, ethanol, propanol, butanol, isopropanol and tert-butanol. These alcoholates are preferably used in the form of the corresponding alcoholic solution. The strongly alkaline substances used are in particular alkali metals or strongly basic compounds thereof, preferably amides, hydrides or alcoholates of alkali metals or mixtures thereof, in particular sodium alcoholates or sodium amides and in particular sodium amide.

Preferably, sodium compounds or potassium compounds are used, of which the hydroxides, alcoholates and amides are of practical importance. Of particular importance is the use of freshly prepared sodium amide. To this end, for example, sodium is added to an initial charge of liquid ammonia, preferably in the presence of a suitable catalyst, such as iron(II) chloride or iron(II) nitrate.

The strongly alkaline substances mentioned are preferably used in anhydrous form, either on their own or as a mixture. However, small amounts of water such as are present in some strong technical grade bases do not interfere in the condensation. The strong bases have widely differing solubilities in liquid ammonia. For example, amides are highly soluble in liquid ammonia while hydroxides only have low solubility. Depending on the type of base used, it is sometimes advantageous to use small amounts of a protic auxiliary solvent. The protic solvents used are water or, preferably, open-chain, branched or cyclic low-molecular-weight aliphatic alcohols having 1 to 8 carbon atoms. However, of particular practical importance is the use of methanol as auxiliary solvent, since the majority of the hydroxides used are highly soluble in methanol.

The amount of base used can vary within wide limits. However, it is preferred to use at least two to three equivalents of base per equivalent of a compound of the formula (2). To carry out the condensation, the reactor is first charged with a compound of the formula (2), and the base is metered thereto during or after metered addition of the compound of the formula (3). Preferably, the reactor is first charged with the compounds of the formulae (2) and (3), and the base is then metered thereto.

After the condensation reaction, excess base can be neutralized by addition of acid compounds. Examples of acid compounds are hydrogen chloride, sulfuric acid and ammonium chloride.

The ratio of the starting products of the formulae (2) and (3) is preferably 1:2 to 1:2.5 and particularly preferably 1:2.1 to 1:2.2.

A particular advantage of the process according to the invention is the ease with which the product can be separated off from the byproducts. Thus, the condensation product of the formula (1) is present as an insoluble compound and can be separated off by filtration. In contrast, the phosphoric ester formed as a byproduct and the further byproducts of the reaction remain dissolved in the liquid ammonia. The liquid ammonia used as solvent can then be purified of all impurities by evaporation and recondensation and be reused.

The distyrylbiphenyl compounds thus obtained are usually used for the fluorescent whitening of textile material, such as cotton, polyamide and wool, or for the fluorescent whitening of paper. To this end, they can be incorporated in liquid and solid detergents, application liquors or coating compositions.

For this purpose, they are usually diluted to the optimum concentration for the particular application by addition of further auxiliaries or water.

The formulations thus obtained can additionally contain customary formulating aids, such as dispersants, builders, protective colloids, stabilizers, preservatives, perfumes, pigments, enzymes and sequestering agents.

The dispersants used are preferably nonionic ones, for example fatty alcohols, ethoxylation products of fatty alcohols or fatty acids, or anionic ones, such as condensation products of aromatic sulfonic acids with formaldehyde, for example those based on sulfonic acids of ditolyl ether or naphthalenesulfonates, or ligninsulfonates.

Examples of builders or protective colloids are modified polysaccharides derived from cellulose or heteropolysaccharides, such as xanthan, carboxymethylcellulose and aluminium silicates or magnesium silicates.

Examples of further auxiliaries which can be added for stabilization are ethylene glycol, propylene glycol and further dispersants.

Examples of compounds which are used as preservatives are 1,2-benzisothiazolin-3-one, formaldehyde or chloroacetamide.

The examples which follow illustrate the invention without limiting it thereto.

EXAMPLE 1

An apparatus set up in series comprises, in the order given:
- a first 1-1 BUECHI ® glass autoclave equipped with a cooling/heating mantle, a manometer (0 to 10 bar) and TESCOM ® back-pressure regulator (0 to 7 bar), a stirrer driven by a permanent magnet, a thermometer sleeve, an inlet port for liquid ammonia and sodium and a bursting disc (10 bar),
- a second 1.5-1 BUECHI ® glass autoclave equipped with a cooling/heating mantle, a manometer (0 to 10 bar) and TESCOM ® back-pressure regulator (0 to 7 bar), a stirrer driven by a permanent magnet, a thermometer sleeve, an inlet port for liquid ammonia and sodium amide/ammonia suspension, bottom outlet valve and a bursting disc (10 bar) and
- a 2-1 LIGACON ® high-pressure autoclave filter equipped with a cooling/heating mantle, a manometer (0 to 10 bar) and TESCOM ® back-pressure regulator (0 to 7 bar), a stirrer driven by a permanent magnet, a thermometer sleeve, an inlet port for the suspension of the reaction product, sintered-metal plate having a pore size of 10 micron and a cloth-covered SEITZ ® filter Ko 0, bottom outlet valve connected to the second glass autoclave and a bursting disc 10 bar.

This apparatus is operated as follows:

The first glass autoclave is charged with 130 g of liquid ammonia at −10° C. (4.2 bar). The autoclave is cooled to −40° C. and let down to atmospheric pressure. After addition of a piece of about 0.5 g of sodium and of 0.5 g of iron(III) nitrate nonahydrate, a total of 15.5 g (0.676 mol) of sodium is added in small portions at this temperature with stirring over a period of 20 minutes, during which a hydrogen stream escapes from the reaction mixture. About 10 minutes after addition of sodium is complete, the autoclave is sealed, and the resulting grey-black sodium amide suspension is stirred at 11° C. (5.8 bar) for another 30 minutes.

The second glass autoclave is charged with 105.7 g of 4,4'-bis(dimethoxyphosphonomethyl)biphenyl (98% of active substance; 0.26 mol) and 148.8 g of sodium benzaldehyde-2-sulfonate (80% of active substance; 0.572 mol) at atmospheric pressure. The autoclave is sealed, cooled to 12° C., and 210 g of liquid ammonia are metered in at this temperature over a period of 5 minutes with stirring to give a pale yellow suspension. This suspension is cooled to 6° C. (4.3 bar), and the sodium amide suspension from the first glass autoclave is metered in over a period of 10 minutes with stirring, which increases the reaction temperature from 6° C. to 14° C. and produces a yellow, crystalline suspension of the reaction product.

The first autoclave is rinsed twice with 50 g each of liquid ammonia, the rinsing solutions are metered into the second glass autoclave, and the reaction mixture is finally stirred at 11° C. (5.8 bar) for one hour. Excess sodium amide is then neutralized by addition of 6 g (0.156 mol) of gaseous hydrogen chloride, the reaction mixture is cooled to 6° C. and introduced into the high-pressure autoclave filter at 6° C. The second glass autoclave is rinsed twice with 50 g each of liquid ammonia, the rinsing solutions being metered into the high-pressure autoclave filter. The reaction mixture is first stirred until it is homogeneous and then filtered off with suction at 6° C. (5.6 bar) at a superatmospheric pressure of 1.5 bar without stirring, the filtrate being introduced into the second glass autoclave. The filter material is suspended twice in 100 g each time of liquid ammonia at 6° C. with stirring, and the suspension is filtered off with suction without stirring, the filtrates being introduced into the second autoclave.

The pressure in the high-pressure autoclave filter and in the second glass autoclave is lowered to atmospheric pressure by partial evaporation of the ammonia, and the filter material and the filtrate residue are largely freed from ammonia by slow heating of the two autoclaves to 20° C. The two autoclaves are emptied, and the filter material and the filtrate residue are heated to 100° C. under vacuum and dried to constant weight.

This gives 153.7 g of disodium 4,4'-bis(2-sulfostyryl)-biphenyl in the form of a pale yellow crystalline powder having a melting point of more than 300° C. and an active substance content (determined by UV spectrophotometry) of 88.6%. The yield of disodium 4,4'-bis(2-sulfostyryl)biphenyl is 93.1% of theory. The filtrate residue (123 g of a light yellow, crystalline, hygroscopic product) mainly consists of dimethyl sodium phosphate.

Analogously to Example 1, the following distyryl compounds of the formulae (8)–(12) are obtained from the corresponding starting materials:

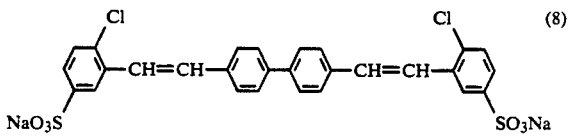

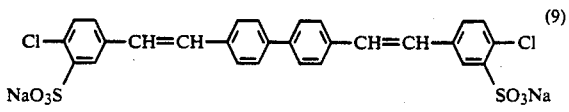

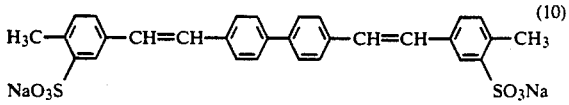

-continued

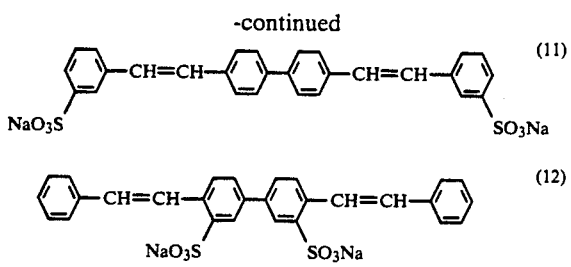

(11), (12)

EXAMPLE 2

Example 1 is repeated, using only a 7% excess of sodium benzaldehyde-2-sulfonate instead of the 10% excess, i.e. 144.8 g (80% of active substance; 0.556 mol).

This gives 154.8 g of disodium 4,4'-bis(2-sulfostyryl)-biphenyl in the form of a light yellow crystalline powder having a melting point of more than 300° C. and an active substance content (measured by UV spectrophotometry) of 88.5%. The yield of disodium 4,4'-bis(2-sulfostyryl)biphenyl is 93.7% of theory. The filtrate residue (79.1 g of a light yellow, crystalline, hygroscopic product) mainly consists of dimethyl sodium phosphate.

EXAMPLE 3

Example 1 is repeated, using only a 5% excess of sodium benzaldehyde-2-sulfonate instead of the 10% excess, i.e. 142.1 g (80% of active substance; 0.546 mol).

This gives 148.8 g of disodium 4,4'-bis(2-sulfostyryl)-biphenyl in the form of a light yellow crystalline powder having a melting point of more than 300° C. and an active substance content (measured by UV spectrophotometry) of 89.0%. The yield of disodium 4,4'-bis(2-sulfostyryl)biphenyl is 90.5% of theory. The filtrate residue (110.9 g of a light yellow, crystalline, hygroscopic product) mainly consists of dimethyl sodium phosphate.

EXAMPLE 4

An apparatus set up as a cascade and comprising, in the following order:
- a first 0.75-1 reaction vessel equipped with a cooling-/heating mantle, stirrer, thermometer and bottom valve,
- a second 1-1 reaction vessel equipped with a cooling-/heating mantle, stirrer, thermometer and bottom valve,
- a 2-1 SEITZ ® pressure filter equipped with a cooling/heating mantle, thermometer, manometer and bottom valve and
- a third 0.75-1 reaction vessel equipped with a cooling-/heating mantle, stirrer, thermometer and bottom valve, is cooled to −40° C.

The first reaction vessel is charged with 140 g of liquid ammonia at −40° C. After addition of a piece of about 0.5 g of sodium and of 0.4 g of iron(III) nitrate nonahydrate, a total of 8.6 g (0.374 mol) of sodium is then added in small pieces at this temperature over a period of 20 minutes with stirring, as a result of which a hydrogen stream escapes from the reaction vessel. The resulting grey-black sodium amide suspension is stirred at −40° C. for another 30 minutes.

The second reaction vessel is charged in the following order with 67.9 g of 4,4'-bis(dimethoxyphosphonomethyl)biphenyl (88% of active substance; 0.15 mol), 89.8 g of sodium benzaldehyde-2-sulfonate (80% of active substance; 0.345 mol) and 280 g of liquid ammonia, and the mixture is stirred.

The sodium amide suspension from the first reaction vessel is metered into this yellow suspension over a period of 5 minutes with stirring, during which the reaction temperature rises from −40° C. to −34° C. and a red suspension is formed. The reaction mixture is then stirred at −40° C. for another 5 hours, a yellow suspension being formed after about 2 hours. Excess sodium amide is neutralized by addition of 4 g of ammonium chloride (0.075 mol).

The reaction mixture is introduced into the pressure filter and filtered off with suction at −40° C. at a superatmospheric pressure of 1.5 bar of nitrogen through a cloth-covered SEITZ ® filter Ko 3. The filter material is washed twice with 100 g each of liquid ammonia and largely freed from ammonia by passing a gentle nitrogen stream through it while simultaneously increasing the temperature of the cooling/heating mantle from −40° C. to +26° C.

The filtrate in the third reaction vessel is also largely freed from ammonia by increasing the temperature of the cooling/heating mantle from −40° C. to +26° C. The filter material and the filtrate residue are finally heated to 100° C. in vacuo and dried to constant weight.

This gives 105.3 g of disodium 4,4'-bis(2-sulfostyryl)-biphenyl in the form of a light yellow crystalline powder having a melting point of more than 300° C. and an active substance content (determined by UV spectrophotometry) of 75.8%. The yield of disodium 4,4'-bis(2-sulfostyryl)biphenyl is 94.6% of theory. The filtrate residue (57.8 g of a light brown, crystalline, hygroscopic product) mainly consists of dimethyl sodium phosphate.

EXAMPLE 5

Example 4 is repeated, using only a 12% excess of sodium benzaldehyde-2-sulfonate instead of the 15% excess, i.e. 87.5 g (80% of active substance; 0.336 mol).

This gives 104.8 g of disodium 4,4'-bis(2-sulfostyryl)-biphenyl in the form of a light yellow crystalline powder having a melting point of more than 300° C. and an active substance content (determined by UV spectrophotometry) of 76.2%. The yield of disodium 4,4'-bis(2-sulfostyryl)biphenyl is 94.5% of theory. The filtrate residue (53.7 g of a light brown, crystalline, hygroscopic product) mainly consists of dimethyl sodium phosphate.

EXAMPLE 6

An apparatus set up in series and comprising, in the following order:
- a first 1-1 BUECHI ® glass autoclave equipped with a cooling/heating mantle, a manometer (0 to 10 bar) and TESCOM ® back-pressure regulator (0 to 7 bar), a stirrer driven by a permanent magnet, a thermometer sleeve, an inlet port for liquid ammonia and sodium and a bursting disc (10 bar), and
- a second 1.6-1 BUECHI ® glass autoclave equipped with a cooling/heating mantle, a manometer (0 to 10 bar) and TESCOM ® back-pressure regulator (0 to 7 bar), a stirrer driven by a permanent magnet, a thermometer sleeve, an inlet port for liquid ammonia and sodium amide/ammonia suspension and a bursting disc 10 bar was operated as follows:

The first glass autoclave is charged with 130 g of liquid ammonia at −10° C. (4.2 bar). The autoclave is cooled to −45° C. and let down to atmospheric presstare. After addition of a piece of about 0.5 g of sodium and of 0.7 g of iron(III) nitrate nonahydrate, a total of 14.4 g (0.625 mol) of sodium is added in small pieces at this temperature over a period of 20 minutes with stirring, as a result of which a hydrogen stream escapes from the reaction mixture. The autoclave is sealed about 10 minutes after sodium addition is complete, and the resulting grey-black sodium amide suspension is stirred at 12° C. (6.1 bar) for another 30 minutes.

The second glass autoclave is charged under atmospheric pressure with 113.2 g of 4,4'-bis(dimethoxyphosphonomethyl)biphenyl (88% of active substance; 0.25 mol) and 142.4 g of sodium benzaldehyde-2-sulfonate (80.4% of active substance; 0.55 mol). The autoclave is sealed, cooled to 0° C., and 210 g of liquid ammonia are metered in at this temperature with stirring, giving a yellow suspension. The sodium amide suspension from the first glass autoclave is metered into this suspension over a period of 15 minutes with stirring, during which the reaction temperature rises from 0° C. (4.1 bar) to 9° C. (5.7 bar) and a yellow, crystalline suspension of the reaction product is formed. The first autoclave is rinsed once with 50 g of liquid ammonia, and the rinsing solution is metered into the second glass autoclave. The reaction mixture is then stirred at 10° C. for another hour, and excess sodium amide is finally neutralized by addition of 5 g (0.125 mol) of gaseous hydrogen chloride.

For workup, the pressure in the second glass autoclave is lowered from 6.4 bar to atmospheric pressure by partial evaporation of the ammonia, as a result of which the internal temperature drops from +10° C. to −30° C., the reaction mixture is diluted with 500 ml of water, and the resulting suspension is largely freed from ammonia by slow heating to +20° C. The stirrer is turned off, and the autoclave is emptied.

The reaction mixture is evaporated to dryness on a rotary evaporator under vacuum, the residue is taken up at about 90° C. in a solution of 81 g of sodium chloride in 375 ml of water, and the mixture is cooled to room temperature. The reaction product is filtered off with suction, washed with 250 ml of a 7.5% sodium chloride solution, heated to 100° C. under vacuum and dried to constant weight.

This gives 141.7 g of disodium 4,4'-bis(2-sulfostyryl)-biphenyl in the form of a light yellow crystalline powder having a melting point of more than 300° C. and an active substance content (determined by UV spectrophotometry) of 93.2%. The yield of disodium 4,4'-bis(2-sulfostyryl)biphenyl is 93.9% of theory.

EXAMPLE 7

Example 6 is repeated, using only a 7% excess of sodium benzaldehyde-2-sulfonate instead of the 10% excess, i.e. 138.5 g (80.4% of active substance; 0.535 mol).

This gives 148.4 g of disodium 4,4'-bis(2-sulfostyryl)-biphenyl in the form of a light yellow crystalline powder having a melting point of more than 300° C. and an active substance content (determined by UV spectrophotometry) of 90.9%. The yield of disodium 4,4'-bis(2-sulfostyryl)biphenyl is 95.9% of theory.

EXAMPLE 8

Example 6 is repeated, taking up the two starting materials 4,4'-bis(dimethoxyphosphonomethyl)biphenyl and sodium benzaldehyde-2-sulfonate in 260 g of liquid ammonia instead of in 210 g.

This gives 147.1 g of disodium 4,4'-bis(2-sulfostyryl)-biphenyl in the form of a light yellow crystalline powder having a melting point of more than 300° C. and an active substance content (determined by UV spectrophotometry) of 91.4%. The yield of disodium 4,4'-bis(2-sulfostyryl)biphenyl is 95.6% of theory.

EXAMPLE 9

An apparatus comprising a 1-1 BUECHI® glass autoclave equipped with a cooling/heating mantle, a manometer (0 to 10 bar) and TESCOM® back-pressure regulator (0 to 7 bar), a stirrer driven by a permanent magnet, a thermometer sleeve, an inlet port and bursting disc (10 bar) is cooled to −45° C.

This glass autoclave is charged with 320 g of liquid ammonia at −45° C., and, after addition of a piece of about 0.5 g of sodium and of 0.3 g of iron(III) nitrate nonahydrate, a total of 5.8 g (0.25 mol) of sodium is added in small pieces over a period of 20 minutes with stirring, during which a hydrogen stream escapes from the reaction vessel. The resulting grey-black sodium amide suspension is stirred at −45° C. for another 30 minutes.

40.7 g of 4,4'-bis(dimethoxyphosphonomethyl)biphenyl (98% of active substance; 0.1 mol) are metered into this sodium amide suspension at −45° C. to −38° C. over a period of 5 minutes by means of a metered powder funnel with stirring, resulting in the formation of a dark red suspension which is stirred at −45° C. for another 30 minutes. 50.5 g of sodium benzaldehyde-2-sulfonate (99% of active substance; 0.24 mol) are then metered into this dark red suspension at −45° C. to −33° C. over a period of 5 minutes by means of a metered powder funnel with stirring.

The glass autoclave is sealed, and the dark red suspension is stirred at −10° C. (2 bar) for another 4 hours, as a result of which the dark red colour disappears and a crystalline light yellow suspension of the reaction product is formed. Excess sodium amide is then neutralized by addition of 2 g (0.05 mol) of gaseous hydrogen chloride.

For workup, the pressure in the glass autoclave is lowered from 2 bar to atmospheric pressure by partial evaporation of the ammonia, as a result of which the internal temperature drops from −10° C. to −33° C. The reaction mixture is diluted with 300 ml of water, and the suspension obtained is largely freed from ammonia by slow heating to +20° C. The stirrer is turned off, and the autoclave is emptied. The reaction mixture is finally evaporated to dryness on a rotary evaporator under vacuum, the residue is taken up at about 90° C. in a solution of 30 g of sodium chloride in 150 ml of water, and the resulting mixture is cooled to room temperature. The reaction product is filtered off with suction, washed with 100 ml of a 7.5% sodium chloride solution and dried at 100° C. under vacuum to constant weight.

This gives 52.5 g of disodium 4,4'-bis(2-sulfostyryl)-biphenyl in the form of a light yellow crystalline powder having a melting point of more than 300° C. and an active substance content (determined by UV spectrophotometry) of 91.4%. The yield of disodium 4,4'-bis(2-sulfostyryl)biphenyl is 85.3% of theory.

EXAMPLE 10

Example 9 is repeated, carrying out the condensation at −35° C. and under atmospheric pressure.

This gives 54.1 g of disodium 4,4'-bis(2-sulfostyryl)-biphenyl in the form of a light yellow crystalline powder having a melting point of more than 300° C. and an active substance content (determined by UV spectrophotometry) of 89.2%. The yield of disodium 4,4'-bis(2-sulfostyryl)biphenyl is 85.8% of theory.

EXAMPLE 11

The apparatus described in Example 9 is charged, in the following order, with 67.8 g of 4,4'-bis(dimethoxyphosphonomethyl)biphenyl (88.1% of active substance; 0.15 mol), 90.6 g of sodium benzaldehyde-2-sulfonate (79.3% of active substance; 0.345 mol) and 230 g of liquid ammonia, and the mixture is stirred at 9° C. (6 bar).

81.0 g of a methanolic 30% sodium methoxide solution (0.45 mol) are metered into this pale yellow suspension over a period of 10 minutes with stirring, as a result of which the reaction temperature rises from 9° C. (6 bar) to 20° C. (6.6 bar) and a crystalline yellow suspension of the reaction product is formed. The reaction mixture is stirred at 20° C. for another hour, and excess sodium methoxide is then neutralized by addition of 6 g (0.15 mol) of gaseous hydrogen chloride.

For workup, the pressure in the glass autoclave is lowered from 6.6 bar to atmospheric pressure by partial evaporation of the ammonia, as a result of which the internal temperature drops from 20° C. to −19° C. The reaction mixture is diluted with 300 ml of water, and the suspension obtained is largely freed from ammonia by slow heating to +20° C. The stirrer is turned off, and the autoclave is emptied. The reaction mixture is finally evaporated to dryness on a rotary evaporator under vacuum, the residue is taken up at about 90° C. in a solution of 45 g of sodium chloride in 225 ml of water, and the resulting mixture is cooled to room temperature. The reaction product is filtered off with suction, washed with 150 ml of a 7.5% sodium chloride solution and dried at 100° C. under vacuum to constant weight.

This gives 83.6 g of disodium 4,4'-bis(2-sulfostyryl)biphenyl in the form of a light yellow crystalline powder having a melting point of more than 300° C. and an active substance content (determined by UV spectrophotometry) of 94.0%. The yield of disodium 4,4'-bis(2-sulfostyryl)biphenyl is 93.1% of theory.

EXAMPLE 12

Example 11 is repeated, using only a 10% excess of sodium benzaldehyde-2-sulfonate instead of the 15% excess, i.e. 86.6 g (79.3% of active substance; 0.33 mol).

This gives 83.2 g of disodium 4,4'-bis(2-sulfostyryl)biphenyl in the form of a light yellow crystalline powder having a melting point of more than 300° C. and an active substance content (determined by UV spectrophotometry) of 94.7%. The yield of disodium 4,4'-bis(2-sulfostyryl)biphenyl is 93.4% of theory.

What is claimed is:

1. A process for preparing distyrylbiphenyl compounds of the formula (1)

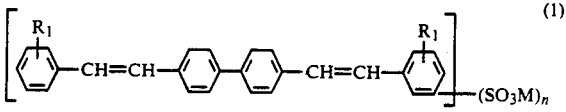

by condensation of a compound of the formula (2)

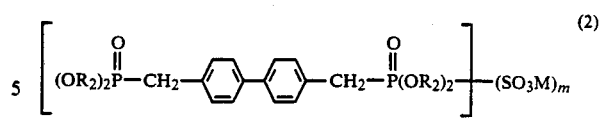

with a compound of the formula (3)

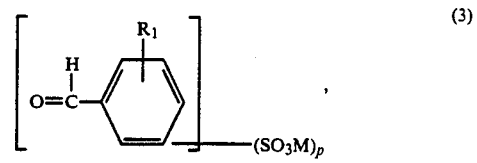

in which $R_1$ is hydrogen, $C_1$-$C_5$alkyl or halogen;
$R_2$ is $C_1$-$C_8$alkyl;
M is a salt-forming colourless cation;
n is 2 or 4;
m is 0 or 2; and
p is 0 or 1; provided m+p is 2 or 4,
which comprises carrying out the condensation in liquid ammonia in the presence of strongly alkaline substances.

2. A process according to claim 1, wherein a compound of the formula (4)

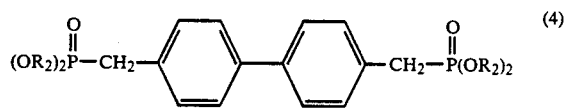

is condensed with a compound of the formula (5)

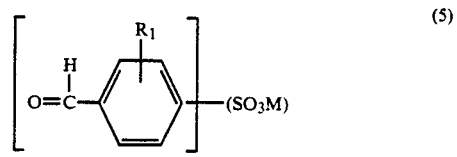

in which $R_1$ is hydrogen, $C_1$-$C_5$alkyl or halogen; $R_2$ is $C_1$-$C_8$alkyl; and
M is a salt-forming colourless cation.

3. A process according to claim 2, wherein a compound of the formula (4) is condensed with a compound of the formula (6)

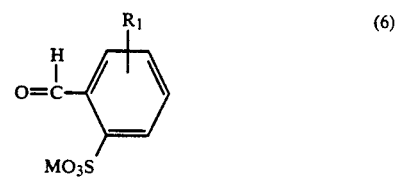

in which $R_1$ is hydrogen, $C_1$-$C_5$alkyl or chlorine;
$R_2$ is $C_1$-$C_8$alkyl; and
M is a salt-forming colourless cation.

4. A process according to claim 1, wherein alkali metals or strongly basic compounds thereof are used as the strongly alkaline substances.

5. A process according to claim 4, wherein amides, hydrides or alcoholates of alkali metals or mixtures thereof are used as the strongly basic compounds.

6. A process according to claim 5, wherein sodium alcoholates or sodium amides are used as the strongly basic compounds.

7. A process according to claim 6, wherein sodium amide is used as the strongly basic compound.

8. A process according to claim 7, wherein the sodium amide used is prepared by dissolving sodium in liquid ammonia in the presence of a catalyst.

9. A process according to claim 1, wherein the condensation is carried out at temperatures of between −40° C. and 25° C.

10. A process according to claim 9, wherein the condensation is carried out at temperatures of between 0° C. and 25° C.

11. A process according to claim 10, wherein the condensation is carried out at temperatures of between 10° C. and 20° C.

12. A process according to claim 1, wherein the compound of the formula (1) is separated off from the by-products by filtration from the liquid ammonia.

13. A process according to claim 1, wherein the ammonia is recycled.

14. A process according to claim 1, wherein the ratio of the compounds of the formulae (2) and (3) is 1:2 to 1:2.5.

15. A process according to claim 14, wherein the ratio of the compounds of the formulae (2) and (3) is 1:2.1 to 1:2.2.

16. A process according to claim 1 for preparing the compounds of the formula (7)

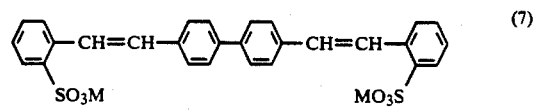

by condensation of a compound of the formula (4)

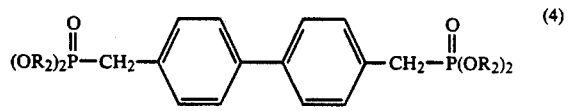

with a compound of the formula (8)

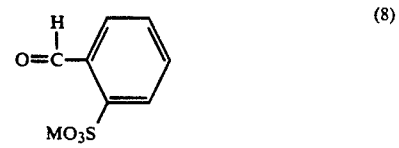

in which $R_2$ is $C_1$–$C_8$alkyl and M is a sodium ion, potassium ion or ammonium ion, wherein
   a) liquid ammonia is introduced as the initial charge;
   b) sodium and a catalyst are added;
   c) the sodium amide suspension thus obtained is metered into a suspension of the compounds of the formula (4) and (8) in liquid ammonia;
   d) excess sodium amide is neutralized;
   e) the end product of the formula (7) is filtered off; and
   f) the ammonia is recovered by evaporation and recondensation.

* * * * *